United States Patent [19]

Adler

[11] 4,141,903
[45] Feb. 27, 1979

[54] PROCESS FOR THE PRODUCTION OF 2-ARYL-2H-BENZOTRIAZOLES

[75] Inventor: Arnold S. Adler, Greenville, R.I.

[73] Assignee: Ciba-Geigy Corporation, Ardsley, N.Y.

[21] Appl. No.: 825,358

[22] Filed: Aug. 17, 1977

[51] Int. Cl.$^2$ ............................................. C07D 249/20
[52] U.S. Cl. ................................................. 260/308 B
[58] Field of Search ..................................... 260/308 B

[56] References Cited

U.S. PATENT DOCUMENTS 3,978,074  8/1976  Jancis ................................. 260/308 B

*Primary Examiner*—Paul M. Coughlan, Jr.
*Attorney, Agent, or Firm*—Luther A. R. Hall

[57] ABSTRACT

A process for the production of 2-aryl-2H-benzotriazoles comprises reducing and cyclizing the corresponding o-nitroazobenzenes with carbon monoxide at a temperature in the range of about 20° C. to about 150° C. and at a pressure in the range of about 15 psia (1 atmosphere) to about 1000 psia (66 atmospheres) in an alkaline medium at a pH over 10 in the presence of a copper-amine complex catalyst. High yields of pure product are obtained with a concomitant reduction of undesired by-products and a reduction in effluent pollution problems.

21 Claims, No Drawings

PROCESS FOR THE PRODUCTION OF 2-ARYL-2H-BENZOTRIAZOLES

BACKGROUND OF THE INVENTION

This invention pertains to a process for the preparation of 2-aryl-2H-benzotriazoles and derivatives thereof. More particularly, the invention relates to a novel process for preparing 2-aryl-2H-benzotriazoles whereby high yields of the desired products are obtained and effluent pollution problems occurring with present processes for making such products are essentially eliminated.

Heretofore, the conversion of an ortho-nitroazobenzene to the corresponding 2-aryl-2H-benzotriazole has been accomplished by chemical and electrolytic reduction processes. For example, as seen in U.S. Pat. Nos. 3,072,585 and 3,230,194, o-nitroazobenzene derivatives have been chemically reduced utilizing zinc in alcoholic sodium hydroxide solutions to give good yields of the corresponding 2-aryl-2H-benzotriazoles. Ammonium sulfide, alkali sulfides, zinc with ammonia at 80°-100° C., sodium hydrosulfide and zinc with hydrochloric acid have also been used as the chemical reducing agents for this transformation as disclosed in U.S. Pat. No. 2,362,988. The use of ammonium sulfide was also reported by S. N. Chakrabarty et al, *J. Indian Chem. Soc.*, 5, 55 (1928); *Chem. Abst.*, 23, 836, (1929) with mixed results depending on the presence or absence of substituent groups on the 2-aryl group. In some cases the desired 2-aryl-2H-benzotriazoles were not formed at all with the products of reduction being only the corresponding o-aminoazobenzenes.

Electrolytic reduction of o-nitroazobenzenes was reported by H. Itomi, *Mem. Coll. Sci. Kyoto Imp. Univ.*, 12A, No. 6, 343 (1929); *Chem. Abst.*, 24, 2060 (1930) with the use of a copper cathode in dilute sodium hydroxide solution. Yields varied from 25 to 60% depending on specific embodiments and conditions with a major impurity being formed, namely the corresponding o-aminoazobenzene.

The widely used zinc dust and sodium hydroxide chemical reducing system for transforming o-nitroazobenzenes into the corresponding 2-aryl-2H-benzotriazoles was reported by K. Elbs, et al, *J. Prakt. Chem.*, 108, 204 (1924); *Chem. Abst.*, 19, 514 (1925). The yields of the desired 2-aryl-2H-benzotriazoles varied from 30 to 85% depending on the specific o-nitroazobenzene intermediate reduced.

The known chemical and electrolytic reduction processes for preparing 2-aryl-benzotriazoles are not practical or economically attractive in many cases. The widely used zinc dust and sodium hydroxide system produces effluent pollution problems in respect to waste disposal of zinc sludge which is of increasing environmental concern.

This increased environmental concern has led to development of several new processes for preparing the 2-aryl 2H-benzotriazoles where pollution problems are mitigated.

In U.S. Pat. No. 4,001,266 the use of hydrazine hydrate was disclosed as a method of preparing the 2-aryl-2H-benzotriazoles by reduction of the corresponding o-nitroazobenzene or N-oxide intermediates.

The preparation in good yield of the isomeric, but chemically distinct 1H-benzotriazoles by the catalytic reduction in alkaline medium of o-nitrophenylhydrazine and selected phenyl ring substituted alkyl and perfluoroalkyl derivatives thereof was reported in Japanese patent publication, Sho 48-26012, Aug. 3, 1973. The isomeric 2H-benzotriazoles of this invention cannot be prepared from phenylhydrazines.

However, the 2-aryl-2H-benzotriazoles were prepared by the catalytic hydrogenation of the o-nitroazobenzene intermediates with hydrogen and various hydrogenation catalysts such as the noble metals, nickel and the like as seen in U.S. Pat. No. 3,978,074.

While hydrogen has classically been used in organic syntheses as a reducing agent involving a minimum of product isolation, pollution and other practical problems, another gaseous reducing agent, namely carbon monoxide, has been largely neglected.

In U.S. Pat. No. 1,237,828 the reduction of nitrobenzene to aniline is reported using a mixture of carbon monoxide and steam at high temperature (200°-220° C.) and a mixed catalyst. Hydrogen is generated under these conditions, however.

Aromatic nitro compounds such as nitrobenzene are converted into the corresponding isocyanates by reaction with carbon monoxide at high temperatures and pressures in the absence of hydrogen and water. Various catalysts are used to aid this reaction as seen in Netherlands Patent 64/10490 where noble metal catalyst and 280 atmospheres pressure is used; in U.S. Pat. No. 3,576,836 where palladious halide plus an organonitrile is used as catalyst at pressures of carbon monoxide of over 100 atmospheres (see also F. J. Weigert, *J. Org. Chem.*, 38, 1316 (1973)); in U.S. Pat. No. 3,461,149 where a noble metal plus a Lewis acid such as ferric or aluminum chloride catalyst is used with pressures of carbon monoxide over 1000 psi (67 atmospheres) (see also W. B. Hardy, et al, *Tetrahedron Letters*, 11, 961 (1967)); in U.S. Pat. No. 3,523,962 where noble metals plus organophosphorus catalysts and pressures of carbon monoxide over 33 atmospheres are used.

When such reactions are carried out in the presence of an alcohol, the isocyanate formed is converted in situ to a urethane as seen in Netherlands Patent 65/02601 and U.S. Pat. No. 3,338,956.

When nitrobenzene is reacted with carbon monoxide over an alumina catalyst at normal pressure, nitrosobenzene and azobenzene are formed while at higher pressure azobenzene is the main product. F. Glaser, et al *Chem. Ing. Tech.* 29, 512 (1957); *Chem. Abst.* 51, 17023h (1957) reports that water should be excluded as it promotes side reactions.

The effect of high pressure reactions of carbon monoxide on various aryl nitrogen compounds in the absence of a catalyst or a source of hydrogen atoms is reported by G. D. Buckley, et al *J. Chem. Soc.*, 1949, 1154. It was found that nitrobenzene, nitrosobenzene and azoxybenzene are each reduced to azobenzene by use of carbon monoxide alone at pressures over 2500 atmospheres at temperatures over 200° C. and in the absence of a catalyst.

J. E. Kmiecik, *J. Org. Chem.* 30, 2014 (1965) reported that various aryl nitro compounds are reduced to either azobenzenes or to the corresponding amine compounds in the presence of carbon monoxide at high pressures (over 70 atmospheres) and at high temperatures (over 200° C.) in the presence of iron pentacarbonyl.

The reduction of nitroalkanes to oximes is disclosed by J. F. Knifton, *J. Org. Chem.* 38, 3296 (1973), (German Offen. 2,019,261), using copper salts solubilized in alkylpolyamines in the presence of carbon monoxide.

Highly basic amines are preferred such as 1,3-propanediamine and 1,6-hexanediamine.

The reduction of nitrobenzene to aniline is reported in U.S. Pat. No. 3,290,377 by use of carbon monoxide at pressures up to 100 atmospheres in the presence of copper salt-amine complex catalysts at moderate temperatures. The yield of aniline was very dependent on the nature and concentration of the copper salt-amine complex catalyst.

The prior art disclosure of reductions of aromatic nitro compounds using carbon monoxide is largely limited to the simple reduction of nitrobenzenes to the corresponding azobenzenes or anilines. There is no teaching that a simultaneous reduction and cyclization of o-nitroazobenzenes to 2-aryl-2H-benzobriazoles are possible or feasible using this special reducing agent. Indeed it is taught that olefinic double bonds are unaffected by the use of the copper salt-amine catalyst/carbon monoxide reduction system.

It is therefore an object of this invention to provide a novel process for the preparation of 2-aryl-2H-benzotriazoles avoiding severe pollution and environmental problems.

A further object of this invention is to prepare 2-aryl-2H-benzotriazoles by reducing and cyclizing the corresponding o-nitroazobenzene under certain conditions hereinafter set forth in greater detail whereby high yields of the products can be obtained in acceptable purity.

DETAILED DISCLOSURE

Taken in its broadest aspect, this invention pertains to a process for the production of 2-aryl-2H-benzotriazoles which comprises reducing and cyclizing the corresponding 2-nitroazobenzene intermediates with carbon monoxide in the presence of a complex metal-amine catalyst in an alkaline medium and recovering the desired 2-aryl-2H-benzotriazoles.

The instant process can be conveniently carried out in an aqueous alkaline organic medium.

A further embodiment of this invention is found in a process for the production of 2-(2-hydroxy-5-methylphenyl)-2H-benzotriazole which comprises treating 2-nitro-2'-hydroxy-5'-methylazobenzene with carbon monoxide at a temperature in the range of from about 20° C. to about 150° C. and at a pressure in the range of about 15 psia (1.05 kg/cm², 1 atmosphere) to about 1,000 pounds per square inch (about 70 kg/cm², 66 atmospheres) in an aqueous alkaline organic medium in the presence of a copper-amine complex catalyst, diluting the reaction mixture, which may optionally contain an additional organic solvent for the o-nitroazobenzene starting material, with water, separating the organic layer, distilling the organic solvent and recovering the desired 2-(2-hydroxy-5-methylphenyl)-2H-benzotriazole by conventional procedures.

The complex copper-amine catalyst of value in the instant process has been found useful in the carbon monoxide reduction of simple organic nitro compounds such as nitrobenzene and nitroalkanes. The high selectivity of this catalyst-reduction system in reducing nitro groups to amino groups is pointed out in U.S. Pat. No. 3,290,377. Surprisingly, application of this reduction system to o-nitroazobenzenes does not lead to o-aminoazobenzenes, but rather to 2-aryl-2H-benzotriazoles. The complex copper-amine catalyst/carbon monoxide reduction system also does not remove halogen groups which may be present in the o-nitroazobenzene intermediates during the reductive cyclization reaction to the 2-aryl-2H-benzotriazoles.

The complex copper-amine catalyst comprises an aqueous or organic solution of a copper-amine complex. The copper compound is in the cupric (II) state with an anion selected from the group consisting of oxide, hydroxide, carbonate and an anionic residue of an organic acid. The amine is an organic amine or ammonia having a $pK_a$ value of at least 9.5 and giving an aqueous solution with a pH of at least 10. The complex copper-amine catalysts are described in some detail in U.S. Pat. No. 3,290,377, the essential material of said Specification being incorporated herein by reference.

The copper compounds useful in preparing the complex copper-amine catalysts are selected from the group consisting of copper oxide, copper hydroxide, copper carbonate and the copper salts of weak organic acids such as copper acetate, copper formate, copper benzoate and copper propionate.

The preferred copper compound is copper acetate or copper carbonate. Particularly preferred is copper acetate.

Copper salts of strong mineral acids or copper cyanide are less effective in forming active copper-amine catalysts than are the aforementioned copper compounds.

While the instant process preferably uses a copper-amine complex catalyst, it is also contemplated that good yields of the desired 2-aryl-2H-benzotriazoles may be obtained by the use in the instant process of a metal salt or metal carbonyl compound-amine complex catalyst wherein the metal is selected from those of groups IB, IIB, VB, VIB, VIIB and VIII of the periodic table. The useful catalysts would be those containing copper, silver, gold, vanadium, chromium, molybdenum, tungsten, iron, ruthenium, osmium, cobalt, rhodium, iridium, nickel, palladium and platinum. Especially useful would be those of iron, cobalt, nickel, silver as well as copper.

The amines which are effective all are relatively strong bases. The main characteristics of the amines, useful in the present invention, are that they form complexes with the copper compounds, that they have $pK_a$ values over 9.5 and that their aqueous solutions have a pH of at least 10. The amines useful in preparing the copper-amine catalyst have the general formula

$$R^6-NH-R^7$$

wherein $R^6$ is hydrogen; or when $R^7$ is alkyl of 1 to 6 carbon atoms, $R^6$ is hydrogen or alkyl of 1 to 6 carbon atoms; $R^7$ is hydrogen, alkyl of 1 to 6 carbon atoms, β-hydroxyethyl, $-(CH_2)_nNH_2$ where $n$ is 4 to 6, or $-(C_xH_{2x}NH)_y(C_xH_{2x})NH_2$ where $x$ is 2 or 3 and $y$ is 0 to 3; or $R^6$ and $R^7$ together are alkylene of 4 to 5 carbon atoms.

Examples of amines of formula $R^6-NH-R^7$ useful in preparing the copper-amine catalyst are 1,3-propanediamine, 1,2-propanediamine, n-hexylamine, ethanolamine, ammonia, piperidine, pyrrolidine, diethylamine, dimethylamine, 1,6-hexanediamine, 3,3'-iminobispropylamine, ethylenediamine, diethylenetriamine, triethylenetetramine and tetraethylenepentamine. Particularly preferred are 1,3-diaminopropane and piperidine.

The more volatile amines such as ammonia and the lower alkylamines should be used under pressure conditions to assure their solubility in the reaction mixture in proper concentrations.

The catalyst complex is composed of at least two moles of amine per mole of copper compound and preferably the amine is used in large excess. The excess amine may also serve as a solvent.

The minimum amount of catalyst complex required for reduction of the o-nitroazobenzenes, calculated on the basis of the copper compound, is 0.05 mol per mol of o-nitroazobenzene. Preferably for obtaining reasonable reaction times a minimum of 0.2 mol of catalyst complex per mol of o-nitroazobenzene should be used. Larger amounts can be used without detriment. In continuous operations quite large excesses of catalyst complex to o-nitroazobenzene may be used advantageously.

The copper-amine complex as formed is in the cupric valence state (II) and the complex is inactive till after treatment with carbon monoxide which activates the catalyst by first reducing the copper present to the cuprous state.

This activation process can be followed by watching the initial deep blue color of the initial cupric complex disappear as carbon monoxide converts the copper into the cuprous valence state. Air and other oxidizing systems should be prevented from coming in contact with the activated copper (I)-amine complex.

The o-nitroazobenzene intermediates to be reduced by the carbon monoxide in the presence of an aqueous solution of a copper-amine complex are relatively high molecular weight aromatic compounds of very low water solubility. In order to facilitate the reductive cyclization reaction, the o-nitroazobenzene intermediate is conveniently dissolved in a solvent.

The organic solvents which may be used in this process to dissolve the o-nitroazobenzene intermediates and corresponding 2-aryl-2H-benzotriazoles can be non-polar hydrocarbon solvents such as benzene, toluene, xylene, cyclohexane, aliphatic hydrocarbons, such as hexane, heptane, petroleum mineral spirits and other hydrocarbon materials and mixtures thereof. For reasons of economy, ease of operation and availability, toluene or xylene is particularly useful in the process of this invention.

Water-miscible polar solvents or cosolvents are also useful in this invention. They include the water-miscible alcohols such as methanol, ethanol, isopropanol, n-propanol, n-butanol and methyl cellosolve (2-methoxyethanol).

Other water-miscible solvents or cosolvents useful in this process include ethers such as tetrahydrofuran, 1,4-dioxane, 1,2-dimethoxyethane, 1,2-diethoxyethane and the like.

Other solvents found useful in this process include the trialkyl phosphates such as triethyl phosphate, tributyl phosphate and the like.

The choice of solvent will be dictated by economics of operation, reaction conditions, solubility considerations of the o-nitroazobenzene intermediates and isolation procedures for the 2-aryl-2H-benzotriazole.

Use of the hydrocarbon solvents leads to a facile method for isolating the 2H-benzotriazole. Upon completion of the reductive cyclization reaction, the reaction mixture is diluted with water and the desired product is separated into the organic layer. The amine and copper components of the catalyst are present in the aqueous phase from which they can be isolated and recycled.

The desired 2H-benzotriazole is easily isolated in crude form as the still pot residue after vacuum distillation of the separated organic phase in yields in the range of 60-90%. The crude product may be further purified by one of several procedures to give purified products of high purity in yields in the range of 55-85%. A variety of trace by-products are formed during the reduction of o-nitroazobenzenes. These include the corresponding o-aminoazobenzenes, o-aminohydrazobenzenes, o-phenylenediamine, anilines, aminophenols and 1,2,3-benzotriazoles. Most of these by-product impurities are removed by an acid, preferably sulfuric acid, wash followed by an alcohol, preferably isopropanol, wash and finally a water wash of the crude 2H-benzotriazole product. Alternatively, the crude product may be dissolved in an organic solvent, such as toluene, and the impurities extracted by an aqueous acid solution, and the product isolated then from organic solution by conventional procedures.

The process of this invention can be carried out at a temperature of from about 20° C. to about 150° C., preferably from about 50° C. to about 120° C., and most preferably from about 75° C. to about 100° C. When temperatures over 100° C. are used, it is necessary to use superatmospheric pressure or to use reactants and solvents with boiling points higher than the reaction temperatures contemplated.

Generally the reaction is carried out at atmospheric pressure or at pressures up to about 1000 psia. Elevated pressures are useful to increase the solubility of the carbon monoxide in the reaction mixture as well as to maintain ammonia or lower alkylamines when ammonia or a lower alkylamine is used in the copper-complex catalyst in reactions run at higher temperatures. The instant reaction, however, is very conveniently run at atmospheric pressure by bubbling carbon monoxide through the reaction mixture at moderate temperatures (75°-100° C).

The reduction of o-nitroazobenzenes to the corresponding 2-aryl-2H-benzotriazoles is a two-step process as outlined below:

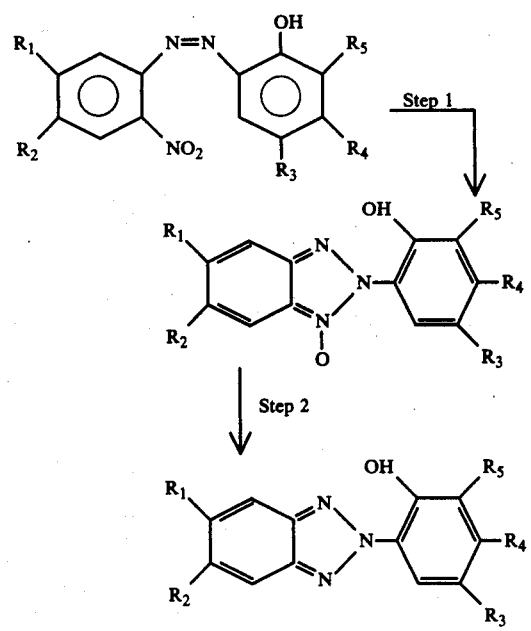

Step 1 — The reduction of the o-nitroazobenzene to the N-oxybenzotriazole derivative proceeds rapidly and exothermically even at low temperature under the process conditions of this invention.

Step 2 — The reduction of the N-oxybenzatriazole intermediate to the corresponding 2-aryl-2H-benzotriazole product goes more slowly. This reduction can be greatly expedited by adding more catalyst, raising the temperature, increasing the carbon monoxide pressure or by combination of these factors.

Generally, the reaction ceases when the N-oxy intermediate is completely reduced to the corresponding 2-aryl-2H-benzotriazole making for facile control of this catalytic reduction process.

Specifically, the instant invention provides an improved process for production of compounds having the formula I

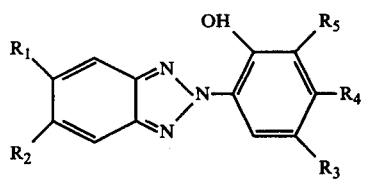

wherein
$R_1$ is hydrogen or chlorine,
$R_2$ is hydrogen, chlorine, lower alkyl of 1 to 4 carbon atoms, lower alkoxy of 1 to 4 carbon atoms, carboalkoxy of 2 to 9 carbon atoms, carboxy or —$SO_3H$,
$R_3$ is alkyl of 1 to 12 carbon atoms, alkoxy of 1 to 4 carbon atoms, phenyl, phenyl substituted with alkyl groups, said alkyl groups having 1 to 8 carbon atoms, cycloalkyl of 5 to 6 carbon atoms, carboalkoxy of 2 to 9 carbon atoms, chlorine, carboxyethyl or phenylalkyl of 7 to 9 carbon atoms,
$R_4$ is hydrogen, lower alkyl of 1 to 4 carbon atoms, lower alkoxy of 1 to 4 carbon atoms, chlorine or hydroxyl, and
$R_5$ is hydrogen, alkyl of 1 to 12 carbon atoms, chlorine, cycloalkyl of 5 to 6 carbon atoms or phenylalkyl of 7 to 9 carbon atoms.

$R_2$ can be lower alkyl of 1 to 4 carbon atoms such as methyl, ethyl or n-butyl. $R_2$ can also be lower alkoxy of 1 to 4 carbon atoms such as methoxy, ethoxy or n-butoxy. $R_2$ can also be carboalkoxy of 2 to 9 carbon atoms such as carbomethoxy, carboethoxy, or carbo-n-octoxy.

$R_3$ can be alkyl of 1 to 12 carbon atoms such as methyl, ethyl, sec-butyl, tert-butyl, amyl, tert-octyl or n-dodecyl. $R_3$ can also be alkoxy of 1 to 4 carbon atoms such as methoxy, ethoxy or n-butoxy. $R_3$ is also phenyl substituted with alkyl groups, said alkyl groups having 1 to 8 carbon atoms such as methyl, tert-butyl, tert-amyl or tert-octyl. $R_2$ can also be cycloalkyl of 5 to 6 carbon atoms such as cyclopentyl or cyclohexyl. $R_3$ is also carboalkoxy of 2 to 9 carbon atoms such as carbomethoxy, carboethoxy, carbo-n-butoxy or carbo-n-octoxy. $R_3$ is also phenylalkyl of 7 to 9 carbon atoms such as benzyl, α-methylbenzyl or α,α-dimethylbenzyl.

$R_4$ can be lower alkyl of 1 to 4 carbon atoms such as methyl, ethyl or n-butyl.

$R_4$ can also be lower alkoxy of 1 to 4 carbon atoms such as methoxy, ethoxy or n-butyloxy.

$R_5$ can be alkyl of 1 to 12 carbon atoms such as methyl, sec-butyl, tert-butyl, tert-amyl, tert-octyl or n-dodecyl.

$R_5$ can also be cycloalkyl of 5 to 6 carbon atoms such as cyclopentyl or cyclohexyl. $R_5$ is also phenylalkyl of 7 to 9 carbon atoms such as benzyl, α-methylbenzyl or α,α-dimethylbenzyl.

Preferably $R_1$ is hydrogen.
Preferably $R_2$ is hydrogen, chlorine, lower alkyl of 1 to 2 carbon atoms, methoxy or carboxy.
Preferably $R_3$ is alkyl of 1 to 12 carbon atoms cyclohexyl, phenyl, chlorine, α-methylbenzyl or carboxyethyl.
Preferably $R_4$ is hydrogen, hydroxyl or methyl.
Preferably $R_5$ is hydrogen, chlorine, alkyl of 1 to 12 carbon atoms, cyclohexyl, benzyl or α-methylbenzyl.
Most preferably $R_2$ is hydrogen or chlorine.
Most preferably $R_3$ is methyl, tert-butyl, tertamyl, tert-octyl, sec-butyl, cyclohexyl, chlorine or carboxyethyl.
Most preferably $R_4$ is hydrogen.
Most preferably $R_5$ is hydrogen, chlorine, methyl, sec-butyl, tert-butyl, tert-amyl, tert-octyl or α-methylbenzyl.

While the instant process can be used to prepare 2-aryl-2H-benzotriazoles of Formula I by the reduction of the o-nitroazobenzene intermediates of formula II, it is also possible to prepare as a product the compound of step 1 namely the 2-aryl-2H-benzotriazole N-oxide of formula Ia

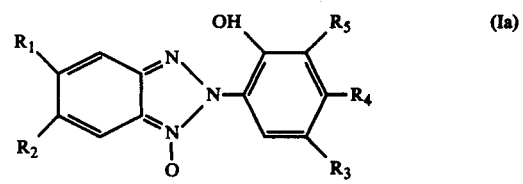

wherein $R_1$, $R_2$, $R_3$, $R_4$ and $R_5$ are as indicated earlier.

By like token one can also start out with the product of step 1 namely the compound of Formula Ia and reduce it using the process of the instant invention to form the desired 2-aryl-2H-benzotriazoles of Formula I.

The process involved the reduction of an o-nitroazobenzene intermediate of the formula II

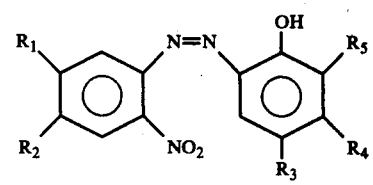

wherein $R_1$, $R_2$, $R_3$, $R_4$ and $R_5$ are as described previously.

The starting o-nitroazobenzene intermediates are prepared by coupling the appropriate o-nitrobenzenediazonium compounds of formula III

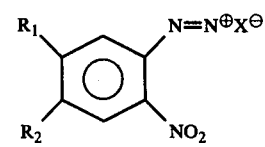

wherein $R_1$ and $R_2$ are as described previously and X is chloride, sulfate, or other anionic species, but preferably chloride, with phenols of formula IV

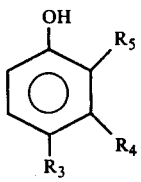

which couple in the ortho position to the hydroxy group.

The o-nitrobenzenediazonium compounds are in turn prepared by standard diazotization procedures using sodium nitrite in acid solution with the corresponding o-nitroanilines of formula V

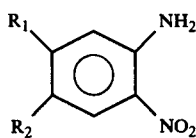

For illustration purposes some specific examples of compounds of formulas IV and V are listed. These items are generally available as items of commerce.

COMPOUNDS OF FORMULA IV p-cresol
2,4-di-tert-butylphenol
2,4-di-tert-amylphenol
2,4-di-tert-octylphenol
2-tert-butyl-4-methylphenol
4-cyclohexylphenol
4-tert-butylphenol
4-tert-amylphenol
4-tert-octylphenol
2,4-dimethylphenol
3,4-dimethylphenol
4-chlorophenol
2,4-dichlorophenol
3,4-dichlorophenol
4-phenylphenol
4-phenoxyphenol
4-o-tolylphenol
4-(4'-tert-octyl)phenylphenol
ethyl 4-hydroxybenzoate
n-octyl 4-hydroxybenzoate
4-methoxyphenol
4-n-octylphenol
4-n-dodecylphenol
resorcinol
4-(α-methylbenzyl)phenol
2-(α-methylbenzyl)-4-methylphenol
2-cyclohexyl-4-methylphenol
4-sec-butylphenol
2-sec-butyl-4-tert-butylphenol
2-tert-butyl-4-sec-butylphenol
4-carboxyethylphenol
2-methyl-4-carboxyethylphenol Preferably compounds of formula IV useful in this invention are
p-cresol
2,4-di-tert-butylphenol
2,4-di-tert-amylphenol
2,4-di-tert-octylphenol
2-tert-butyl-4-methylphenol
4-tert-octylphenol
4-n-octylphenol
4-n-dodecylphenol
resorcinol
2-sec-butyl-4-tert-butylphenol
2-(α-methylbenzyl)-4-methylphenol

COMPOUNDS OF FORMULA V o-nitroaniline
4-chloro-2-nitroaniline
4,5-dichloro-2-nitroaniline
4-methoxy-2-nitroaniline
4-methyl-2-nitroaniline
4-ethyl-2-nitroaniline
n-butyl 3-nitro-4-aminobenzoate
n-octyl 3-nitro-4-aminobenzoate
4-n-butoxy-2-nitroaniline
3-nitro-4-aminobenzoic acid
3-nitro-4-aminobenzenesulfonic acid Preferably compounds of Formula V useful in this invention are
o-nitroaniline
4-chloro-2-nitroaniline The 2-aryl-2H-benzotriazoles have found wide use as dyestuff intermediates, optical brightener blue fluorescent agents and selective ultraviolet light absorbing stabilizers affording valuable protection for fibers, films and a variety of polymeric structures subject to deterioration by ultraviolet radiation. These materials have become important items of commerce.

The 2-aryl-2H-benzotriazoles are complex organic molecules which require careful synthetic procedures for their production in good yield and acceptable purity.

The present invention is concerned with an improved process to prepare ultraviolet stabilizers which are substituted 2-aryl-2H-benzotriazoles. These are distinguished by a very slight adsorption in visible light and very high fastness to light in various substrates. Particularly valuable members of these stabilizers are compounds having a free hydroxyl group in the 2-position of the aryl group linked to the 2-nitrogen of the benzotriazole and which are further substituted in the 3- and 5- or in the 4- and 5-positions by lower alkyl groups and may be substituted by a chlorine in the 5-position of the benzotriazole nucleus.

The description, preparation and uses of these valuable substituted 2-aryl-2H-benzotriazoles are further taught in the U.S. Pat. Nos. 3,004,896, 3,055,896, 3,072,585, 3,074,910, 3,189,615 and 3,230,194.

The compounds of formula IV and formula V as well as the copper compounds, amines and carbon monoxide are all generally available as items of commerce.

The following examples are given to illustrate the process of the present invention, but are not intended to limit the scope of the present invention in any manner whatsoever.

EXAMPLE 1

2-(2-Hydroxy-5-methylphenyl)-2H-benzotriazole

To a 1000-ml. round-bottomed, three-neck flask fitted with a gas inlet tube, stirrer and reflux condenser is added 20.0 grams (0.08 mol) of 2-nitro-2'-hydroxy-5'-methylazobenzene (99.7% pure) dissolved in a solution of 200 ml of xylene. To this solution is added with stirring a mixture of 23.0 grams (0.32 mol) of 1,3-diaminopropane, 100 ml of water and 4 grams (0.02 mol) of cupric acetate. Carbon monoxide gas is then bubbled through the stirred reaction mixture for 15-20 hours with the temperature being maintained at 85°-90° C.

At the end of the reaction period, the reaction mixture is diluted with 200 ml of water, and cooled to room temperature. The organic layer is separated and the xylene solvent removed by vacuum distillation. The still pot residue comprises the crude product in good yield.

The crude product is purified by dissolving in toluene and extracting with 70% aqueous sulfuric acid. The toluene solution is then stirred with Prolit Rapid, an acidic clay, which is then removed by filtration. The clay is washed with toluene, and the combined toluene filtrate is then concentrated by vacuum distillation. After most of the toluene is distilled off, isopropanol is added dropwise to the still-pot residue. The resulting solution is cooled to 0°-5° C. and the resulting crystals are isolated by filtration, washed with cold isopropanol and vacuum dried at 70°—80° C. to give pure product.

EXAMPLE 2 - 9

2-(2-Hydroxy-5-methylphenyl)-2H-benzotriazole

Using the general procedure of Example 1, variations in the solvent, amine copper salt, and reaction temperature are investigated.

| | Effect of Solvent | |
|---|---|---|
| Example | Solvent | Yield Product |
| 1 | xylene | good |
| 2 | toluene | good |
| 3 | ethanol | good |
| 4 | propanol | good |

Substitution of water-miscible polar solvents for the aromatic hydrocarbon xylene of Example 1 still gives the desired product in good yield.

| | Effect of Amine | |
|---|---|---|
| Example | Amine | Yield Product |
| 1 | 1,3-diaminopropane (DAP) | good |
| 5 | Triethanolamine plus pyridine | No reaction |
| 6 | piperidine | good |

The fact that no product is observed when weaker, that is less basic, amines are used is not unexpected. The reduction occurs in this system at a pH of about 10 and the $pK_a$ values of the amines useful in this reaction must be in the range of 9.5 or higher. Both 1,3-diaminopropane ($pK_a = 10.62$) and piperidine ($pK_a = 11.28$) meet this requirement fully.

It is expected that substitution of 1,3-diaminopropane with other amines of like basicity would lead to the production of the desired 2H-benzotriazole.

| | Effect of Copper (II) Salt | |
|---|---|---|
| Example | Cupric Salt | Yield Product |
| 1 | acetate | good |
| 7 | carbonate | good |

The use of several cupric salts both give the desired product in good yield. The choice of cupric compound would be dictated by economics of operation.

| | Effect of Temperature | | |
|---|---|---|---|
| Example | Reaction Temperature ° C | Yield Product | Remarks |
| 1 | 85-90 | good | cupric acetate |
| 8 | 94 | good | cupric acetate |
| 9 | 65-70 | good | cupric acetate |

The reaction appears to proceed well at 85°-90° C. with lower temperatures giving somewhat lower yields of product in the same reaction time. Still higher reaction temperatures are expected to give good yields of the product in shorter reaction times.

EXAMPLE 10

2-(2-Hydroxy-3,5-di-tert-amylphenyl)-2H-benzotriazole

When using the procedure of Example 1 an equivalent amount of 2-nitro-2'-hydroxy-3',5'-di-tert-amylazobenzene is substituted for 2-nitro-2'-hydroxy-5'-methylazobenzene, the above noted product is obtained.

EXAMPLE 11

2-(2-Hydroxy-5-tert-octylphenyl)-2H-benzotriazole

When using the procedure of Example 1 an equivalent amount of 2-nitro-2'-hydroxy-5'-tert-octylazobenzene is substituted for 2-nitro-2'-hydroxy-5'-methylazobenzene, the above noted product is obtained.

EXAMPLE 12

5-Chloro-2-(2-hydroxy-3,5-di-tert-butylphenyl)-2H-benzotriazole

When in Example 1, the 2-nitro-2'-hydroxy-5'-methylazobenzene is replaced by an equivalent amount of 2-nitro-5-chloro-2'-hydroxy-3',5'-di-tert-butylazobenzene, the above noted product is obtained.

It is noted that the copper-amine/carbon monoxide reduction system does not cause loss of the chloro group at the 5 position on the 2H-benzotriazole moiety as does occur when reductive hydrogenation is carried out with palladium catalysts.

EXAMPLE 13

5-Chloro-2-(2-hydroxy-3-tert-butyl-5-methylphenyl)-2H-benzotriazole

When in Example 1, the 2 nitro-2'-hydroxy-5'-methyl-azobenzene is replaced by an equivalent amount of 2-nitro-5-chloro-2'-hydroxy-3'-tert-butyl-5'-methylazobenzene, the above noted product is obtained.

EXAMPLE 14

2-(2-Hydroxy-3,5-di-tert-butylphenyl)-2H-benzotriazole

When in Example 1, the 2-nitro-2'-hydroxy-5'-methylazobenzene is replaced by an equivalent amount of 2-nitro-2'-hydroxy-3,5'-di-tert-butylazobenzene, the above noted compound is obtained.

EXAMPLE 15

2-(2-Hydroxy-5-tert-butylphenyl)-2H-benzotriazole

When in Example 1, the nitro-2'-hydroxy-5'-methylazobenzene is replaced by an equivalent amount of 2-nitro-2'-hydroxy-5'-tert-butylazobenzene, the above named compound is obtained.

EXAMPLE 16

2-(2-Hydroxy-3-sec-butyl-5-tert-butylphenyl)-2H-benzotriazole

When in Example 1, the 2 nitro-2'-hydroxy-5'-methylazobenzene is replaced by an equivalent amount of 2-nitro-2'-hydroxy-3'-sec-butyl-5'-tert-butylazobenzene, the above named product is obtained.

EXAMPLE 17

2-(2-Hydroxy-3-(α-methylbenzyl)-5-methylphenyl)-2H-benzotriazole

When in Example 1, the 2-nitro-2'-hydroxy-5'-methylazobenzene is replaced by an equivalent amount of 2-nitro-2'-hydroxy-3'-(α-methylbenzyl)-5'-methylazobenzene, the above noted product is obtained.

What is claimed is:

1. A process for the production of 2-aryl-2H-benzotriazoles of the formula I.

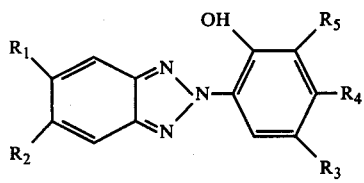

wherein
$R_1$ is hydrogen or chlorine,
$R_2$ is hydrogen, chlorine, lower alkyl of 1 to 4 carbon atoms, lower alkoxy of 1 to 4 carbon atoms or carboalkoxy of 2 to 9 carbon atoms, carboxy or $-SO_3H$,
$R_3$ is alkyl of 1 to 12 carbon atoms, alkoxy of 1 to 4 carbon atoms, phenyl, phenyl substituted with alkyl groups, said alkyl groups having 1 to 8 carbon atoms, cycloalkyl of 5 to 6 carbon atoms, carboalkoxy of 2 to 9 carbon atoms, chlorine, carboxyethyl or phenylalkyl of 7 to 9 carbon atoms,
$R_4$ is hydrogen, lower alkyl of 1 to 4 carbon atoms, lower alkoxy of 1 to 4 carbon atoms, chlorine or hydroxyl, and
$R_5$ is hydrogen, alkyl of 1 to 12 carbon atoms, chlorine, cycloalkyl of 5 to 6 carbon atoms or phenylalkyl of 7 to 9 carbon atoms, which comprises
reducing and cyclizing the corresponding o-nitroazobenzene intermediate (II)

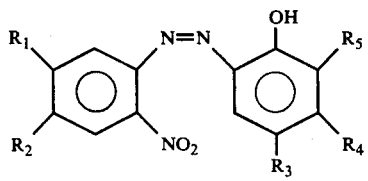

with carbon monoxide at a temperature in the range of from about 20° C. to about 150° C. and at a pressure in the range of from about 15 psia (1.05 kg/cm², 1 atmosphere) to about 1000 psia (70 kg/cm², 66 atmospheres) when mixed in an alkaline medium having a pH greater that 10 in the presence of at least 0.05 mol, per mol of said o-nitroazobenzene intermediate, of a copper compound-amine complex catalyst consisting essentially of (a) a copper compound selected from the group consisting of copper oxide, copper hydroxide, copper carbonate and a copper salt of a weak organic acid, and (b) an amine of the formula $$R^6-NH-R^7$$

wherein $R^6$ is hydrogen; or when $R^7$ is alkyl of 1 to 6 carbon atoms, $R^6$ is hydrogen or alkyl of 1 to 6 carbon atoms;
$R^7$ is hydrogen, alkyl of 1 to 6 carbon atoms, β-hydroxyethyl, $-(CH_2)_nNH_2$ where $n$ is 4 to 6, or $-(C_xH_{2x}NH)_y(C_xH_{2x})NH_2$ where $x$ is 2 or 3 and $y$ is 0 to 3; or $R^6$ and $R^7$ together are alkylene of 4 to 5 carbon atoms, said complex containing at least two mols of said amine per mol of said copper compound, and
recovering the desired 2-aryl-2H-benzotriazole.

2. A process according to claim 1 wherein the copper compound is copper acetate or copper carbonate.

3. A process according to claim 2 wherein the copper compound is copper acetate.

4. A process according to claim 1 wherein the amine is 1,3-diaminopropane or piperidine.

5. A process according to claim 1 for the production of a compound of formula I wherein
$R_1$ is hydrogen,
$R_2$ is hydrogen, chlorine, lower alkyl of 1 to 2 carbon atoms, methoxy or carboxy,
$R_3$ is alkyl of 1 to 12 carbon atoms, cyclohexyl, phenyl, chlorine, α-methylbenzyl or carboxyethyl,
$R_4$ is hydrogen, hydroxyl or methyl, and
$R_5$ is hydrogen, alkyl of 1 to 12 carbon atoms, chlorine, cyclohexyl, benzyl or α-methylbenzyl.

6. A process according to claim 1 for the production of a compound of formula I wherein
$R_1$ is hydrogen,
$R_2$ is hydrogen or chlorine,
$R_3$ is methyl, sec-butyl, tert-butyl, tert-amyl, tert-octyl, methoxy, cyclohexyl, chlorine or carboxyethyl,
$R_4$ is hydrogen, and
$R_5$ is hydrogen, chlorine, methyl, tert-butyl, sec-butyl, tert-amyl, tert-octyl or α-methylbenzyl.

7. A process according to claim 1 for the production of 2-(2-hydroxy-5-methylphenyl)-2H-benzotriazole.

8. A process according to claim 1 for the production of 2-(2-hydroxy-5-tert-octylphenyl)-2H-benzotriazole.

9. A process according to claim 1 for the production of 2-(2-hydroxy-3,5-di-tert-amylphenyl)-2H-benzotriazole.

10. A process according to claim 1 for the production of 2-(2-hydroxy-3,5-di-tert-butylphenyl)-2H-benzotriazole.

11. A process according to claim 1 for the production of 5-chloro-2-(2-hydroxy-3,5-di-tert-butylphenyl)-2H-benzotriazole.

12. A process according to claim 1 for the production of 5-chloro-2-(2-hydroxy-3-tert-butyl-5-methylphenyl)-2H-benzotriazole.

13. A process according to claim 1 wherein the alkaline medium is an aqueous alkaline organic medium.

14. A process for the production of 2-aryl-2H-benzotriazole N-oxides of the formula Ia

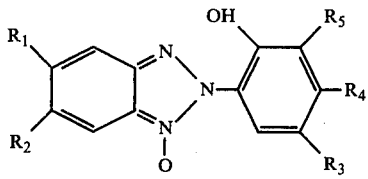

wherein
R₁ is hydrogen or chlorine,
R₂ is hydrogen, chlorine, lower alkyl of 1 to 4 carbon atoms, lower alkoxy of 1 to 4 carbon atoms or carboalkoxy of 2 to 9 carbon atoms, carboxy or —SO₃H,
R₃ is alkyl of 1 to 12 carbon atoms, alkoxy of 1 to 4 carbon atoms, phenyl, phenyl substituted with alkyl groups, said alkyl groups having 1 to 8 carbon atoms, cycloalkyl of 5 to 6 carbon atoms, carboalkoxy of 2 to 9 carbon atoms, chlorine, carboxyethyl or phenylalkyl of 7 to 9 carbon atoms,
R₄ is hydrogen, lower alkyl of 1 to 4 carbon atoms, lower alkoxy of 1 to 4 carbon atoms, chlorine or hydroxyl, and
R₅ is hydrogen, alkyl of 1 to 12 carbon atoms, chlorine, cycloalkyl of 5 to 6 carbon atoms or phenylalkyl of 7 to 9 carbon atoms, which comprises
reducing and cyclizing the corresponding o-nitroazobenzene intermediate (II)

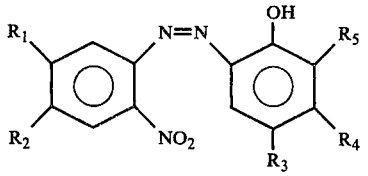

with carbon monoxide at a temperature in the range of from about 20° C. to about 150° C. and at a pressure in the range of from about 15 psia (1.05 kg/cm², 1 atmosphere) to about 1000 psia (70 kg/cm², 22 atmospheres) when mixed in an alkaline medium having a pH greater than 10 in the presence of at least 0.05 mol, per mol of said o-nitroazobenzene intermediate, of a copper compound-amine complex catalyst consisting essentially of (a) a copper compound selected from the group consisting of copper oxide, copper hydroxide, copper carbonate and a copper salt of a weak organic acid, and (c) an amine of the formula

wherein R⁶ is hydrogen, or when R⁷ is alkyl of 1 to 6 carbon atoms, R⁶ is hydrogen or alkyl of 1 to 6 carbon atoms;
R⁷ is hydrogen, alkyl of 1 to 6 carbon atoms, β-hydroxyethyl, —(CH₂)ₙNH₂ where n is 4 to 6, —(CₓH₂ₓNH)ᵧ(CₓH₂ₓ)NH₂ where x is 2 or 3 and y is 0 to 3; or R⁶ and R⁷ together are alkylene of 4 to 5 carbon atoms, said complex containing at least two mols of said amine per mol of said copper compound, and
recovering the desired 2-aryl-2H-benzotriazole N-oxide.

15. A process according to claim 14 wherein the copper compound is copper acetate or copper carbonate.

16. A process according to claim 15 wherein the copper compound is copper acetate.

17. A process according to claim 14, wherein the amine is 1,3-diaminopropane or piperidine.

18. A process for the production of 2-aryl-2H-benzotriazoles of the formula I

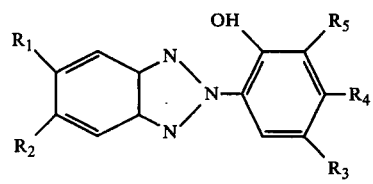

wherein
R₁ is hydrogen or chlorine,
R₂ is hydrogen, chlorine, lower alkyl of 1 to 4 carbon atoms, lower alkoxy of 1 to 4 carbon atoms or carboalkoxy of 2 to 9 carbon atoms, carboxy or —SO₃H,
R₃ is alkyl of 1 to 12 carbon atoms, alkoxy of 1 to 4 carbon atoms, phenyl, phenyl substituted with alkyl groups, said alkyl groups having 1 to 8 carbon atoms, cycloalkyl of 5 to 6 carbon atoms, carboalkoxy of 2 to 9 carbon atoms, chlorine, carboxyethyl or phenylalkyl of 7 to 9 carbon atoms,
R₄ is hydrogen, lower alkyl of 1 to 4 carbon atoms, lower alkoxy of 1 to 4 carbon atoms, chlorine or hydroxyl, and
R₅ is hydrogen, alkyl of 1 to 12 carbon atoms, chlorine, cycloalkyl of 5 to 6 carbon atoms or phenylalkyl of 7 to 9 carbon atoms, which comprises
reducing the 2-aryl-2H-benzotriazole N-oxide intermediate (Ia)

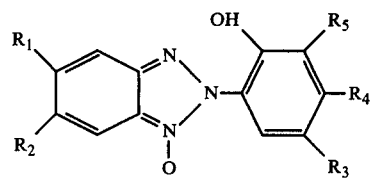

which carbon monoxide at a temperature in the range of from about 20° C. to about 150° C. and at a pressure in the range of from about 15 psia (1.05 kg/cm², 1 atmosphere) to about 1000 psia (70 kg/cm², 66 atmospheres) when mixed in an alkaline medium having a pH greater than 10 in the presence of at least 0.05 mol, per mol of said 2-aryl-2H-benzotriazole N-oxide intermediate, of a copper compound-amine complex catalyst consisting essentially of (a) a copper compound selected from the group consisting of copper oxide, copper hydroxide, copper carbonate and a copper salt of a weak organic acid, and (b) an amine of the formula

wherein R⁶ is hydrogen; or when R⁷ is alkyl of 1 to 6 carbon atoms, R⁶ is hydrogen or alkyl of 1 to 6 carbon atoms;

$R^7$ is hydrogen, alkyl of 1 to 6 carbon atoms, β-hydroxyethyl, $-(CH_2)_n NH_2$ where $n$ is 4 to 6, or $-(C_xH_{2x}NH)_y(C_xH_{2x})NH_2$ where $x$ is 2 or 3 and $y$ is 0 to 3; or $R^6$ and $R^7$ together are alkylene of 4 to 5 carbon atoms, said complex containing at least two mols of said amine per mol of said copper compound, and recovering the desired 2-aryl-2H-benzotriazole.

19. A process according to claim 18 wherein the copper compound is copper acetate or copper carbonate.

20. A process according to claim 19 wherein the copper compound is copper acetate.

21. A process according to claim 18 wherein the amine is 1,3-diaminopropane or piperidine.

* * * * *

UNITED STATES PATENT AND TRADEMARK OFFICE
CERTIFICATE OF CORRECTION

PATENT NO. : 4,141,903
DATED : Feb. 27, 1979
INVENTOR(S) : Arnold S. Adler

It is certified that error appears in the above—identified patent and that said Letters Patent are hereby corrected as shown below:

At Column 15, Line 44 should read as follows:

$kg/cm^2$, 66 atmospheres) when mixed in an alkaline

Signed and Sealed this

Twenty-fourth Day of July 1979

[SEAL]

Attest:

LUTRELLE F. PARKER

Attesting Officer     Acting Commissioner of Patents and Trademarks